(12) United States Patent
Kuzniecky et al.

(10) Patent No.: US 11,191,471 B2
(45) Date of Patent: Dec. 7, 2021

(54) MINIMALLY INVASIVE SUBGALEAL EXTRA-CRANIAL ELECTROENCEPHALOGRAPHY (EEG) MONITORING DEVICE

(71) Applicant: New York University, New York, NY (US)

(72) Inventors: Ruben I. Kuzniecky, Englewood, NJ (US); Werner K. Doyle, New York, NY (US); Steven V. Pacia, New York, NY (US); Daniel Friedman, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/121,714

(22) PCT Filed: Feb. 26, 2015

(86) PCT No.: PCT/US2015/017798
§ 371 (c)(1),
(2) Date: Aug. 25, 2016

(87) PCT Pub. No.: WO2015/130955
PCT Pub. Date: Sep. 3, 2015

(65) Prior Publication Data
US 2017/0035316 A1    Feb. 9, 2017

Related U.S. Application Data

(60) Provisional application No. 61/945,550, filed on Feb. 27, 2014.

(51) Int. Cl.
*A61B 5/0478* (2006.01)
*A61B 5/04* (2006.01)
(Continued)

(52) U.S. Cl.
CPC ............ *A61B 5/291* (2021.01); *A61B 5/0002* (2013.01); *A61B 5/0006* (2013.01); *A61B 5/01* (2013.01);
(Continued)

(58) Field of Classification Search
CPC ............ A61B 5/04; A61B 5/0476; A61B 1/32
(Continued)

(56) References Cited

U.S. PATENT DOCUMENTS 6,006,124 A    12/1999  Fischell et al.
6,353,754 B1    3/2002  Fischell et al.
(Continued)

OTHER PUBLICATIONS

Sperling, Chapter 20, Current Practice of Clinical Electroencephalography, Philadelphia, Wolters Kluwer Health, 2002, pp. 639-679.

*Primary Examiner* — Jon Eric C Morales
(74) *Attorney, Agent, or Firm* — Fay Kaplun & Marcin, LLP (57) ABSTRACT

A system includes an implantable body configured for implantation in a subgaleal extracranial position, the implantable body including a first electrode array including a first elongated body comprising first and second electrode contacts separated from one another by a distance selected to facilitate the detection of brain electrical activity and a unit coupled to the first electrode array. The unit includes a processor analyzing the detected brain electrical activity to determine whether an epileptic event has occurred and generating epileptic event data based on this determination and a transceiver controlled by the processor to wirelessly transmit epileptic event data to and from a remote computing device.

28 Claims, 7 Drawing Sheets

(51) Int. Cl.
  *A61B 5/291*    (2021.01)
  *A61B 5/00*     (2006.01)
  *A61B 5/296*    (2021.01)
  *A61B 5/316*    (2021.01)
  *A61B 5/01*     (2006.01)
  *A61B 5/0205*   (2006.01)
  *A61B 5/0533*   (2021.01)
  *A61B 5/11*     (2006.01)
  *A61B 5/145*    (2006.01)

(52) U.S. Cl.
  CPC ........ *A61B 5/02055* (2013.01); *A61B 5/0533* (2013.01); *A61B 5/11* (2013.01); *A61B 5/14532* (2013.01); *A61B 5/296* (2021.01); *A61B 5/316* (2021.01); *A61B 5/6868* (2013.01)

(58) Field of Classification Search
  USPC .......................................... 600/202, 544–545
  See application file for complete search history.

(56) References Cited

U.S. PATENT DOCUMENTS

| | | |
|---|---|---|
| 6,469,049 B1 | 10/2002 | Meyerhoff et al. |
| 8,140,150 B2 | 3/2012 | Greene |
| 8,396,557 B2 | 3/2013 | DiLorenzo |
| 2006/0173364 A1 | 8/2006 | Clancy et al. |
| 2007/0150025 A1 | 6/2007 | Dilorenzo et al. |
| 2007/0265543 A1 | 11/2007 | VanSickle et al. |
| 2008/0027346 A1 | 1/2008 | Litt et al. |
| 2008/0183097 A1 | 7/2008 | Leyde et al. |
| 2008/0208074 A1* | 8/2008 | Snyder ................ A61B 5/0476 600/545 |
| 2008/0234598 A1 | 9/2008 | Snyder et al. |
| 2010/0016073 A1 | 6/2010 | Shachar et al. |
| 2010/0145176 A1 | 6/2010 | Himes |
| 2010/0331717 A1 | 12/2010 | Pless et al. |
| 2012/0083700 A1 | 4/2012 | Osorio |
| 2012/0209133 A1 | 8/2012 | Beck-Nielsen |
| 2017/0035316 A1 | 2/2017 | Kuzniecky et al. |

\* cited by examiner

MINIMALLY INVASIVE SUBGALEAL EXTRA-CRANIAL ELECTROENCEPHALOGRAPHY (EEG) MONITORING DEVICE

This application is a 371 application of PCT Patent Application Ser. No. PCT/US2015/017798 filed on Feb. 26, 2015, which claims priority to U.S. Provisional Patent Application Ser. No. 61/945,550, filed Feb. 27, 2014, the entire contents of which are hereby incorporated by reference herein.

BACKGROUND

For epilepsy patients, an objective seizure detection method that is safe, accurate and does not interfere with patient activities is critical to advance patient care. Seizure frequency is the most important index for determining and monitoring seizure control. Unfortunately, many patients experiencing seizures lose consciousness or are amnesic while most subtle or non-convulsive seizures may be unobserved or unrecognized. As the majority of current determinations of seizure frequency are based on patient and/or caregiver reports, these determinations represent, at best, a crude estimate of the true frequency. Studies have shown that seizure counts reported by the patients or caregivers can have an error rate as high as 60% which has important implications for therapy. Unrecognized seizures have a major effect on epilepsy clinical trials as the error rate and placebo effect are driven largely by the subjective nature of seizure count. Furthermore, unrecognized seizures increase the risk of cognitive decline, injury and death.

The only objective method to account for seizures is in-patient video Electroencephalography (EEG) or ambulatory EEG recordings. Video EEG studies are inpatient based and thus very expensive and only used for acute situations or for pre-surgical investigations. Current methods for ambulatory scalp EEG recordings are not practical for long-term use and can typically be used for a maximum of 3-4 days. These methods are also limited due to scalp EEG artifacts, battery life or the inability of patients to tolerate scalp electrodes from more than a few days. Implantation of intracranial EEG electrodes for long-term monitoring has been developed for situations where epilepsy surgery is appropriate. However, not only are these highly invasive procedures expensive (generally more than $50,000), they also have a high morbidity rate. Such procedures are indicated only for patients who are candidates for resective epilepsy surgery yet there are vastly more patients who would benefit from such implantable EEG surveillance. Seizure detection systems based on body motion or motor activity, accelerometers or video detectors can only detect major convulsive events and are not implantable, limiting their value as most seizures are non-convulsive in nature and therefore not detectable with changes in motion. There is a long-felt need for a device that can accurately record EEG activity relatively free of artifact for extended periods of time (e.g., months to years) and can detect, recognize and store seizure events in patients without causing discomfort to the patient and without compromising their health and safety.

SUMMARY OF THE INVENTION

The present invention is directed to a system, comprising an implantable body configured for implantation in a subgaleal extracranial position, the implantable body including a first electrode array including a first elongated body comprising first and second electrode contacts separated from one another by a distance selected to facilitate the detection of brain electrical activity and a unit coupled to the first electrode array. The unit includes a processor analyzing the detected brain electrical activity to determine whether an epileptic event has occurred and generating epileptic event data based on this determination and a transceiver controlled by the processor to wirelessly transmit epileptic event data to and from a remote computing device.

In one aspect, a method for capturing brain wave data is provided. The method includes inserting, using a minimally invasive surgical technique, an implantable body into a subgaleal extracranial position with the implantable body positioned along a cranial surface and so that first and second electrode contacts of a first electrode array of the implantable body face the cranium. The method also includes detecting brain electrical activity, and monitoring and analyzing, via a processor, the brain electrical activity to detect epileptic events. The method further includes transmitting epileptic event data corresponding to a detected epileptic event to one of a remote computer, local computer, local base station, cellular phone, portable tablet, personal computing device and cloud storage.

In a further aspect, a method for detecting onset of a seizure in a brain of a patient is provided. The method includes obtaining, from a plurality of electrodes implanted into a subgaleal space of the patient and in contact with a cranial surface of the patient, brain electrical activity data corresponding to electrophysiological signals produced by the brain. The method also includes continuously monitoring and analyzing, via a processor, the brain electrical activity data to identify the onset of the seizure in the brain. The method further includes administering an anti-seizure treatment to the patient when the processor identifies the onset of the seizure in the brain.

These and other aspects of the invention will become apparent to those skilled in the art after a reading of the following detailed description of the invention, including the figures and appended claims.

DETAILED DESCRIPTION

The present invention is directed to a system and method for recording EEG activity and detecting epileptic events over an extended continuous period of time to aid in the diagnosis and treatment of epilepsy. An exemplary device includes one or more electrode arrays configured for subgaleal implantation (i.e., between the galea aponeurotica and the pericranium). Thus, while current devices require drilling through the cranium to implant electrodes directly onto the dura mater or into the subdural space, the exemplary device according to the invention permits implantation extra-cranially, reducing trauma, eliminating the need to expose the brain and significantly limiting adverse side effects and consequences of surgery, as those skilled in the art will understand. Furthermore, for most patients, implantation would occur in the ambulatory surgery setting with minimal recovery time and no inpatient hospital stay. The exemplary electrode strip according to the invention comprises a plurality of contacts separated from one another by a predetermined length selected to provide a predetermine sensitivity reading for detecting ictal activity, as those skilled in the art will understand and as described in greater detail below. The plurality of contacts are formed with one of the same and variable contact surface areas and are arranged in particular patterns, as described in greater detail later on. The electrode strip is a flat, flexible biocompatible array connected to an exemplary battery and electronics compartment configured for long-term (i.e., 12 or more months) implantation. The device further comprises programmable analog and digital electronics configured to monitor long-term brain activity without excessively draining the battery and without excessive power consumption, as will be described in greater detail below. The exemplary device is configured to primarily record electrical brain activity and determine, based on the detected brain activity, whether an epileptic event has occurred. Other biometric measurements such as but not limited to blood oxygenation, arterial pulse, galvanic resistance, motion/acceleration, and electro-myographic measurements, anticipated to augment the primary electrical brain activity measurement may also be incorporated into the exemplary device. Epileptic event data corresponding to the detected epileptic events is stored in an electronic memory provided in the implanted device. The device may further comprise a wireless transmitter and receiver (i.e., a transceiver) to transmit the epileptic event data to an external computing device and/or cloud-based data storage and review services. Transmission of data may occur according to one or more patterns (e.g., routine transmission at predetermined time intervals, location-based (e.g., when in proximity to a base station or appropriate personal smart device), upon being prompted to transmit by a secondary device, etc.) If a time-based transmission is used, the rate of transmission may be programmed into the onboard memory. In one example, the data may be programmed for transmission every 1-7 days as determined based on seizure rates estimated by a clinician. Data from the device may be transmitted to the external computing device periodically to reduce the required memory. The exemplary device according to the invention is adapted for implantation at a cranial vertex or a vicinity thereof, as will be described in greater detail below. It is noted, however, that the other implantation locations on the head are also envisioned within the scope of the invention.

Figure 1:
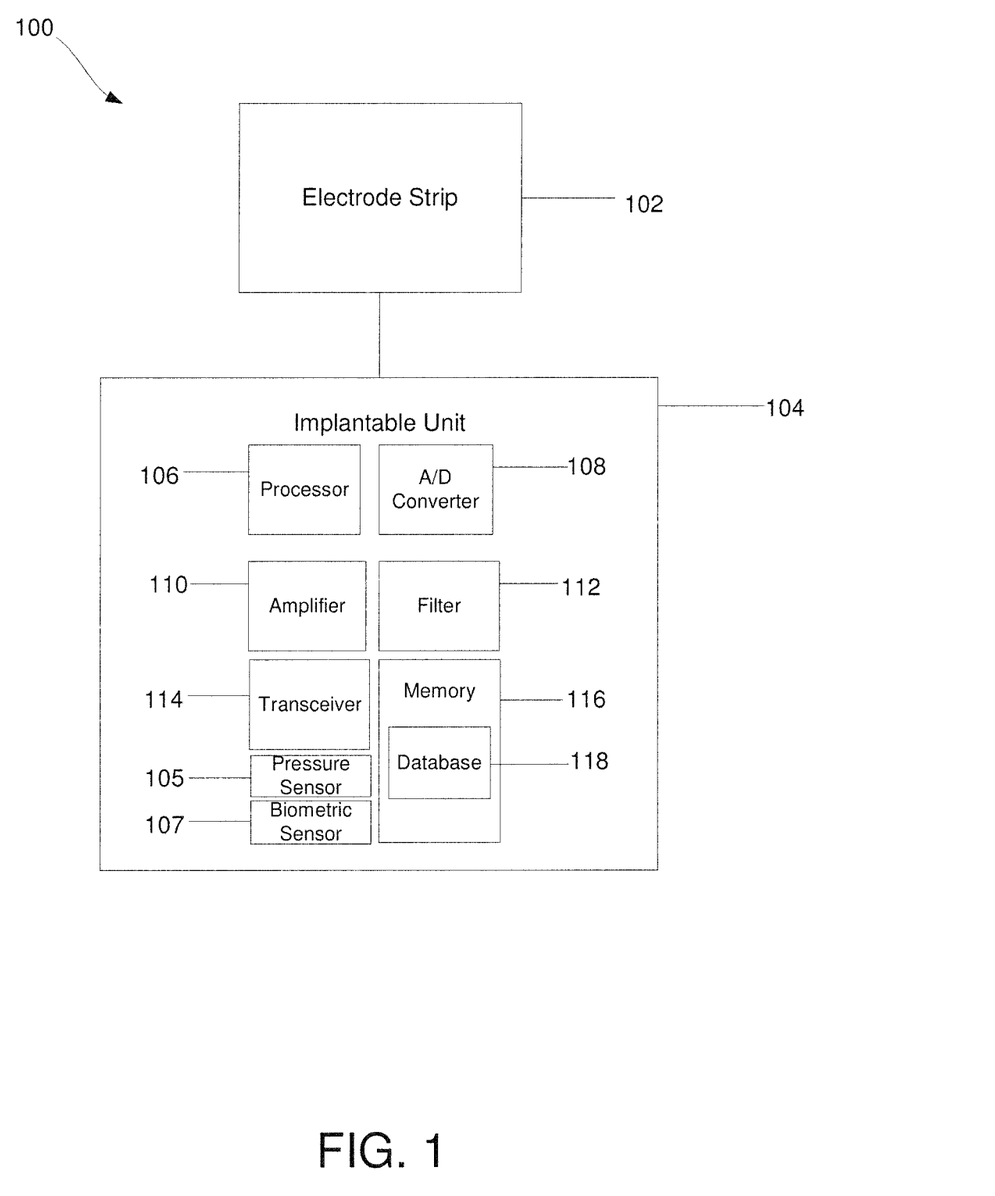
FIG. 1 shows a schematic drawing of an exemplary system according to the invention.
Figure 2:
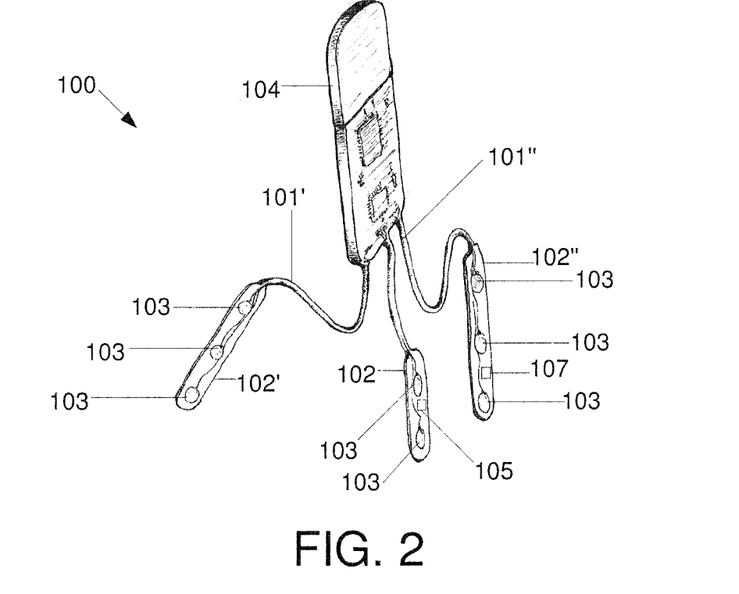
FIG. 2 shows a perspective view of an implantable device according to a first embodiment of the invention.
Figure 3:
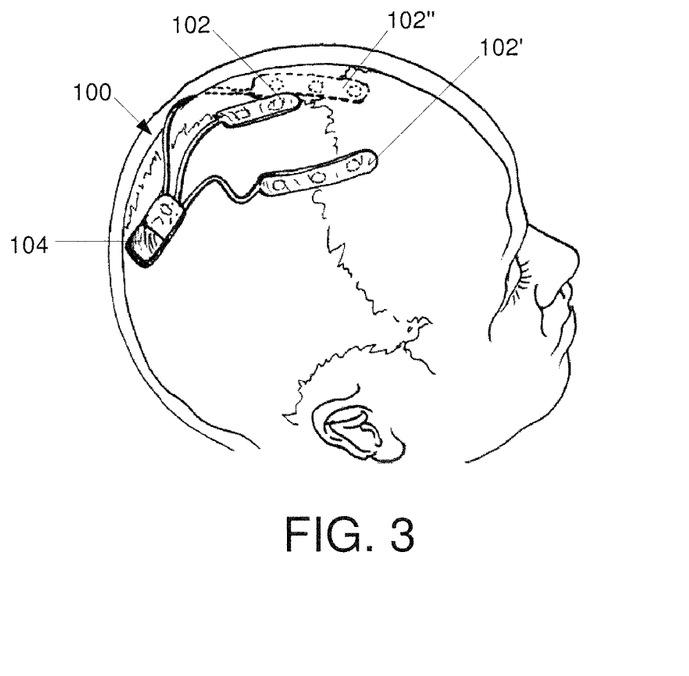
FIG. 3 shows a first view of the device of FIG. 2 in an implanted configuration.
Figure 4:
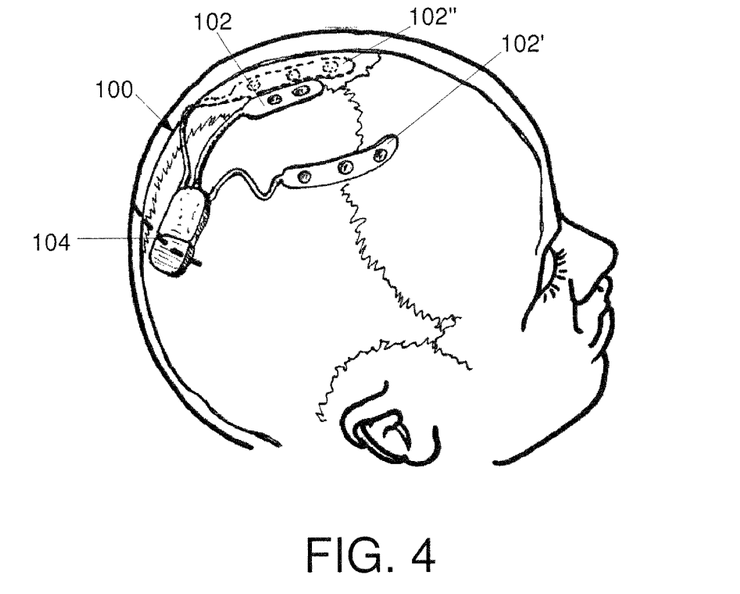
FIG. 4 shows a second view of the device of FIG. 2 in the implanted configuration.

As shown in FIGS. 1-4, an exemplary device 100 according to the invention is dimensioned to permit subgaleal insertion and comprises an implantable unit 104 coupled to one or more low profile electrode arrays 102, 102', 102" by a wire 101, 101', 101". In one embodiment, the device 100 includes three electrode arrays 102, 102', 102". It is noted, however, that any number of arrays 102 may be used without deviating from the scope of the invention. In an exemplary embodiment, each of the arrays 102 is 6-8 cm long, 5-7 mm thick and 0.5-2 cm wide. A first one of the arrays 102 includes two contacts 103 and is connected directly to the implantable unit 104 by a first wire 101 having a first length. Second and third arrays 102', 102" include three contacts 103 and are connected directly to the implantable unit 104 by second and third wires 101', 101" having a second length greater than the first length. As shown in FIGS. 3-4, this configuration permits implantation of the device 100 such that first, second and third arrays 102, 102', 102" are separated from one another. It is noted, however, this embodiment is exemplary only and that any other combination of contacts 103 may be provided on the arrays 102 without deviating from the scope of the invention. The first, second and third arrays 102, 102', 102", respectively, may include 2-6 contacts 103 which may be separated from one another along a length of the arrays 102, 102', 102" by an inter-electrode distance of 1-6 cm. The contacts 103 may be formed of steel, platinum alloy or another conductive material as used for physiological monitoring. The inter-electrode distance is selected to increase sensitivity to ictal activity while minimizing noise. The first, second and third arrays 102, 102', 102", respectively, are reinforced with a flexible mesh or string of a high tensile material embedded therewithin alongside or above the contacts 103 and their associated electrical connections, the reinforcement increasing a strength of the arrays to permit long-term implantation thereof. Any of the arrays 102, 102', 102" may further include one or more pressure sensors 105 on a galeal surface (i.e., a surface located externally of the skull in an implanted configuration) to record pulse and provide a measure of heart rate than can be added to a seizure detection algorithm, as will be described in greater detail later on. It is noted that the placement of the sensor 105 in FIG. 2 is exemplary only and that any number and location of the sensor 105 may be selected without deviating from the scope of the invention. Any of the arrays may further comprise one or more biometric sensors 107 embedded thereon, the biometric sensors 107 capturing one or more of pulse, blood oxygenation data, motion, acceleration, galvanic resistance, temperature, electro-myographic data, pressure and rheologic changes.

In an operative configuration, both the electrode arrays 102, 102', 102" and attached implantable unit 104 are implanted subgallealy. This configuration permits the insertion of the arrays 102, 102', 102" and unit 104 through a single incision in a single outpatient procedure, which reduces risks that are generally encountered by implanting components at different locations in the body. Furthermore, the co-implantation reduces the risk of wire fracture due to the shorter wire length required. The exemplary device 100 produces a negligible amount of functional heat. Any heat produced is readily transferred or dissipated away from the inherent blood perfusion ability of the scalp. Nevertheless, the unit 104 is formed of an insulative material to prevent discharge of heat from the processor. The unit 104 comprises an analog-to-digital converter 108 to convert detected brain wave signals into digital signals at a predetermined sampling rate to adequately record relevant brain activity data. Any number and arrangement of amplifiers 110 and filters 112 are provided to enhance or modify the brain activity data for analysis and detection of specific information. A processor 106 runs a seizure detection algorithm on the brain activity data and identifies epileptic events based on this brain activity data. The processor 106 sends this data to a memory 116 where epileptic event data is stored. The epileptic event data may then be forwarded to a transceiver 114 as for transmission to a remote host (e.g., computer, mobile phone, etc.) via low-energy radio (telemetry) technology. In one embodiment, the processor 106 transmits only epileptic event data to the memory 115 and discards extraneous brain activity data. In an alternative embodiment, the processor 106 transmits epileptic event data wirelessly to a remote host without storage in an attached memory if the remote host is within a predetermined proximity to the patient. In yet another embodiment, the processor 106 saves the epileptic event data to the memory 116 only when the remote host is inaccessible (e.g., when the wearer is not within a transmission range to the remote host). In yet another embodiment, the processor 106 saves epileptic event data to the memory 116 and only transmits the event data to the remote host upon (1) receiving a transmission request from the host, (2) when memory usage reaches a predetermined level, (3) expiration of a predetermined time interval (e.g., daily, weekly, bi-weekly, monthly, etc.) or (4) when a critical number of epileptic events have occurred within a predetermined time period. The memory 116 may further comprise a database 118 containing information necessary for the analysis of brain activity data to detect epileptic events as well as threshold levels and other settings that may be referenced by the processor 106. Once transmitted (off loaded from device memory 116) the data is transferred to and stored locally in a smart device (smart phone), base station, or personal computer, or any other location including, for example, an internet cloud or a specific website. Information associated with the device 100 includes brain electrical data, data corresponding to time of day and circumstances of associated metrics, biometric data (e.g., pulse, body temperature, activity such as motion, etc.) and data captured from one or more pressure sensors 105 or other sensors provided on the arrays 102, 102', 102". Secondary physiologic measures such as heart rate either as a simple metric or as an analyzed time series can be recorded and added to the a seizure detection algorithm. In some embodiments, a warning or alarm may be activated if a potentially dangerous nocturnal seizure is detected.

In accordance with an exemplary method according to the invention, the device 100 is inserted subgalleally using a minimally invasive surgical method, as those skilled in the art will understand, and implanted at a cranial vertex. Specifically, a blunt and tapered tip malleable dissector is passed into the subgaleal space by the surgeon to create a linear pocket into which the electrode arrays 102, 102', 102" are passed. Though the device 100 is typically implanted at the cranial vertex, other implantation locations on the head are also envisioned within the scope of the invention. The exemplary invention has identified the utility of the vertex position in recording seizures arising from and involving multiple brain locations, including the temporal lobes and does not require a priori knowledge of the lateralization of seizures for the individual. Furthermore, the vertex position also allows identification of electrographic markers of sleep stages which are typically maximal over the central head regions allowing a reviewer to easily assess the state during which detected seizures occurred. Finally, the location of the contacts 103 at the vertex, distant to the temporalis muscles reduces the contamination of the captured signal by artifacts produced by chewing or other movements of the jaw muscles. In situations where the precise location of the patient's seizure onsets are known, the implanted arrays 102, 102', 102" can be positioned over the region of the skull closest to this brain region, maximizing the sensitivity of the device to detect the seizure discharge. Furthermore, the exemplary implantation location reduces wound healing time and is cosmetically preferable to other implantation locations. In one embodiment, the implanted device 100 may extend along the axis of the sagittal suture. An orientation of each of the arrays 102, 102', 102" may be selected to correspond to the requirements of the patient. For example, the arrays 102, 102', 102" may be positioned to lie para-sagitally over the vertex of the scalp. After implantation, the device 100 may be optimized by causing the processor to continuously wirelessly transmit a subgaleal EEG signal to enable a surgeon or other user to fine-tune the location and orientation of the device 100 to achieve consistent and high quality brain electrical data or other biometric data. Once implanted, the device 100 monitors the subgaleal EEG continuously throughout the length of implantation via a low-power seizure detection process. In an exemplary embodiment, the device 100 is configured to operate on low-power to permit long-term implantation, wherein the battery powers the device for a period of at least 12 months or a period of up to 12 months or a period greater than 12 months. Due to aging of the electrodes, changes in background activity, or tissue changes such as scarring of adjacent scalp tissue, the baseline signal characteristics such as noise level and signal-to-noise ratio may change for implantable devices during long-term use. The exemplary device 100 is configured to minimize and potentially eliminate the need for any intervention during the implantation period. To address any deterioration of the physiologic signals captured by the device 100, a technique may be implemented to identify and adjust to the changes in the baseline characteristics of the signal by manipulation of impedance or changes in electrode recording position or changes in the electrode sampling (i.e., electrode combination changes that can be programmed into the unit 104 as needed).

Figure 5:
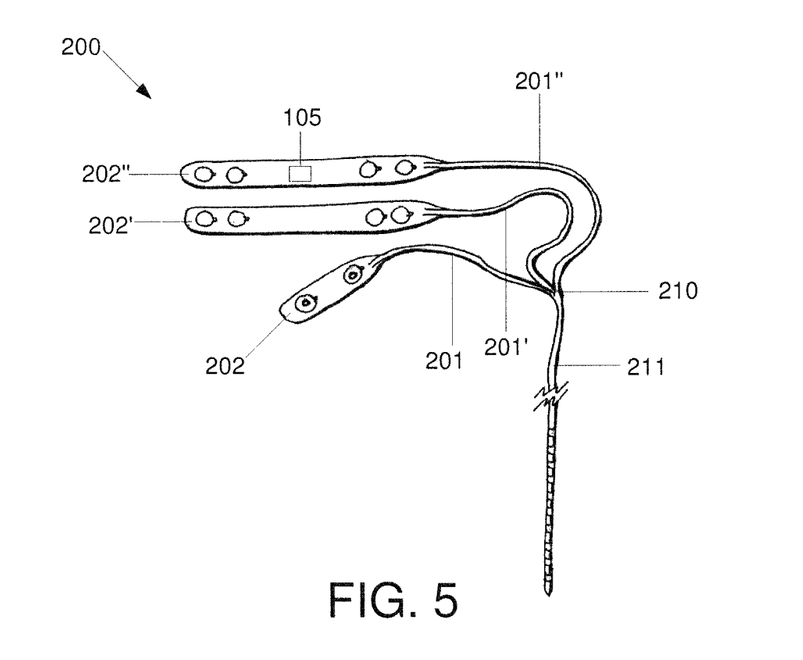
FIG. 5 shows a perspective view of an implantable device according to an alternate embodiment of the invention.

As shown in FIG. 5, a device 200 according to another embodiment of the invention is substantially similar to the device 100 except as noted below. Whereas the arrays 102, 102, 102" of the device 100 are each coupled directly to the implantable unit 104 via wires 101, 101', 101", arrays 202, 202', 202" of the device 200 are connected to the implantable unit 104 (not shown) by a branching connection. Specifically, wires 201, 201', 201" extend from the arrays 202, 202', 202" to a junction 210. A single wire 211 extends from the junction 210 to the unit 104. Each of the wires 201, 201', 201" has a different length so that corresponding arrays 202, 202', 202' are separated from one another in the implanted configuration. In one embodiment, the first wire 201 is 6 cm long and the second and third wires 201', 201" are 8 cm long. It is noted that these measurements are exemplary only and that any other measurements may be used without deviating from the scope of the invention.

In another alternative embodiment shown in FIGS. 6-10, the exemplary device 300 may comprise a composite unit for detecting and analyzing brain activity data. The composite unit is preferably a single integrated device. It is believed that a single integrated device provides improved reliability as compared to multi-part devices. For example, the integrated device 300 requires the use of fewer lengthy leads, which are believed to be a cause of mechanical failure. In this particular embodiment, the exemplary device 300 may be a single integrated device that is in one piece and thereby reduces the number of lengthy leads, and thus, the risk of failure of the device attributable to mechanical failure of such lengthy leads. In addition, it is believed that a single integrated device allows a physician to more easily implant the device in a subgaleal region, and thus, provide for easier removal or revision of the device, shorter surgery time, and/or less invasive surgical procedure to place the device in an operative configuration.

The exemplary device 300 may comprise a low profile electrode strip 302, as show in FIGS. 6-10, which is sized and shaped for insertion into a subgaleal region of a patient. In one exemplary embodiment, the electrode strip 302 may have a length from about 4 cm to about 8 cm. The electrode strip 302 may be a single composite flexible electrode strip having a proximal end 305 and a distal end 306. The electrode strip 302 may be formed from any resiliently flexible material suitable for implantation. For example, the electrode strip 302 may be formed from or reinforced with a flexible mesh or string of a high tensile material.

In one embodiment, the electrode strip 302 may a central axis (L) bisecting the length of the electrode strip. The electrode strip 302 may comprise one or more electrode contacts 303 positioned proximal of the central axis, and one or more electrode contacts 303 distal to the central axis. More particularly, the electrode strip 302 comprises two to four contacts 303 proximal of the central axis, and two to four contacts distal of the central axis. In one particular embodiment, the electrode strip 302 may comprise one or more electrode contacts 303 positioned at or near each of the proximal end 305 and the distal end 306. Preferably, the electrode strip 302 may comprise two to four contacts 303 at or near each of the proximal end 305 and the distal end 306 of the electrode strip 302. The contacts 303 may be formed of steel, platinum alloy or other conductive material suitable for use for physiological monitoring. Preferably, the contacts 303 are formed from stainless steel. The contacts 303 on the electrode strip 302 may be configure to record brain activity data, e.g., EEG data of the patient's brain, by bipolar or referential recording. The inter-electrode distance between contacts 303 at each of the proximal end 305 and the distal end 306 may be each independently selected to increase sensitivity to ictal activity while minimizing noise. The electrode strip 302 may also include one or more pressure sensors on a galeal surface to record pulse and provide a measure of heart rate. In other embodiments, the electrode strip 302 may also comprise one or more biometric sensors capturing one or more of pulse, blood oxygenation data, motion, acceleration, galvanic resistance, temperature, electromyographic data, pressure and rheologic changes.

The contacts 303 on the electrode strip may be connected to an implantable unit 304 by a wire 301. Each contact 303 may be independently connected via a wire 301 to the implantable unit. Alternatively, the contacts 303 may be connected to wires 301 forming a branching connection (not shown) that is connected to the implantable unit 304. The implantable unit 304 may be similar to the implantable unit 104 describe above except as noted below. The implantable unit 304 may include a processor for executing a seizure detection process or algorithm on brain activity data collected by the exemplary device, e.g., contacts 303, and identifying epileptic events based on this brain activity data. The processor may send the data to a memory where epileptic event may be stored. The implantable unit 304 may also include a transceiver for transmitting the epileptic event data to a remote host (e.g., computer, mobile phone, etc.) via low-energy radio (telemetry) technology. Additionally, the implantable unit 304 may comprise an analog-to-digital converter to convert detected brain wave signals into digital signals, preferably at a predetermined sampling rate to adequately record relevant brain activity data. The implantable unit 304 may also include any number and arrangement of amplifiers and filter to enhance or modify the brain activity data for analysis and detection of specific information. The implantable unit 304 may further comprise a battery for powering the components therein, e.g., processor, memory, transceiver, etc. In certain exemplary embodiments, the implantable unit 304 may comprise a flexible battery or a battery that can be separated to articulate with a curvature of a person's skull.

Figure 6:
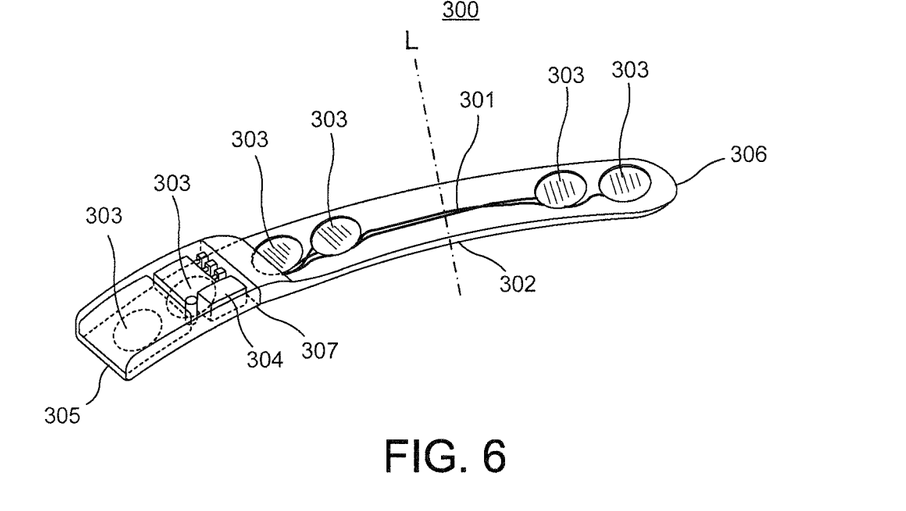
FIG. 6 shows a perspective view of an implantable device according to another embodiment of the invention.

The implantable unit 304 may be positioned at a proximal end 305 of the electrode 302 strip and may be enclosed within a housing 307. As shown in FIG. 6, the housing 307 is hermetically sealed around the implantable unit 304, which includes the battery. In some embodiments, the housing may have a slightly curved shape that corresponds to a mean curvature of a human skull. It is believed that this curved housing shape more closely correlates to a curvature of a patient's skull and thus reduces the chance for skin erosion or breakdown of the exemplary device 300 caused by friction between the device and the patient, such as the patient's skin or skull. In certain embodiments, the housing 308 may be formed of an electrically conductive material. More particularly, the housing 308 may serve as a reference or ground for the exemplary device 300. In other embodiments, the housing 308 may be formed of an insulative material to prevent discharge of heat from the implantable unit 304.

Figure 7:
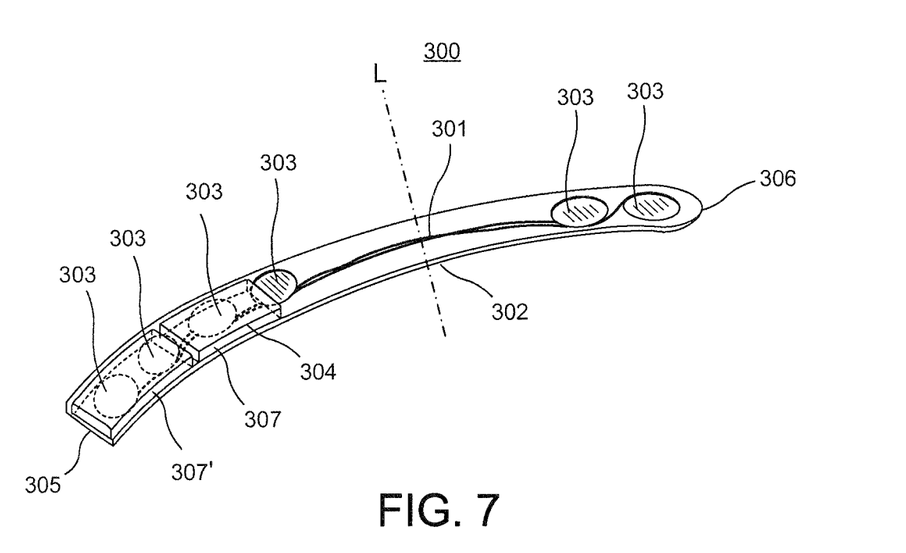
FIG. 7 shows a perspective view of an implantable device according to a further embodiment of the invention.
Figure 8:
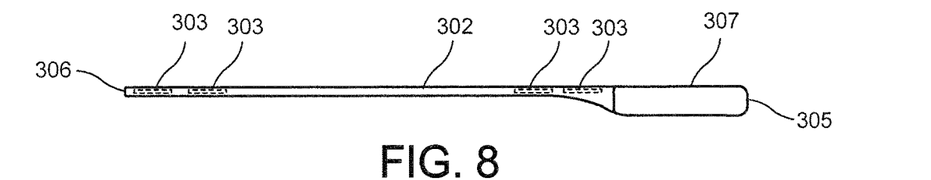
FIG. 8 shows a side view of the device of FIG. 6.
Figure 9:
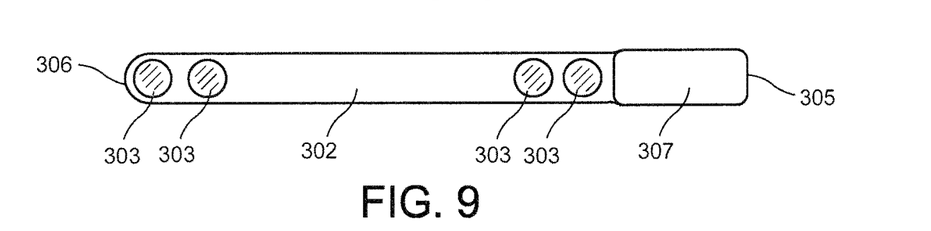
FIG. 9 shows a top view of the device of FIG. 6.

In another embodiment, as shown in FIG. 7 the battery may be separately sealed within a second housing 307' while the remainder of the implantable unit 304 is sealed with housing 307. The second housing 307' may be similar to housing 307 as described above. In some embodiments, the second housing 307' may be proximal of the housing 307. In other embodiments (not shown), the second housing 307' may be distal to the housing 307. The exemplary embodiment shown in FIG. 7 allows for more flexibility at the proximal end 305 of the electrode strip 302. Therefore, the device 300 shown in FIG. 7 provides for more flexibility and can be more closely curved to correspond to the curvature over the patient's skull.

Figure 10:
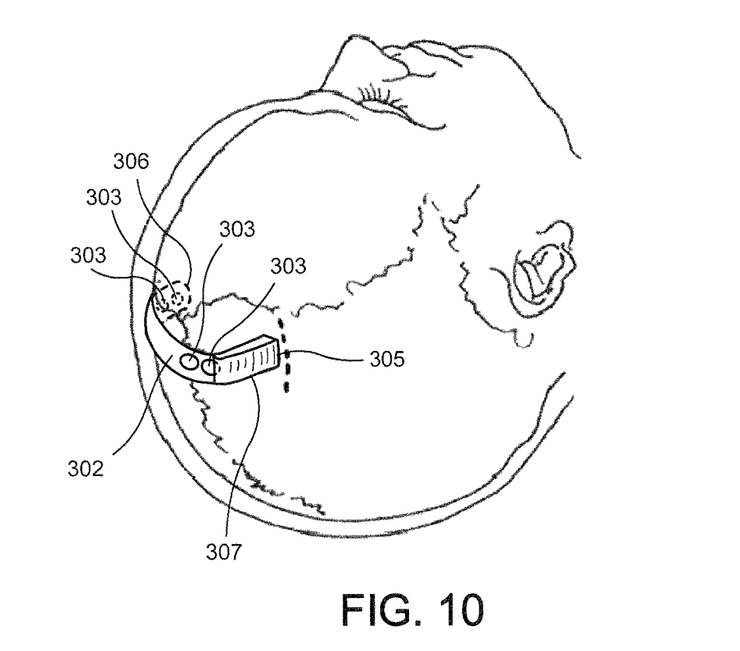
FIG. 10 shows a first view of the device of FIG. 6 in an implanted configuration.

In an operative configuration the device 300 may be implanted subgalleally through a single incision at a cranial vertex of the patient. The device 300 may be placed in any suitable position in a subgaleal region that is between the skull and the scalp of the patient. In certain embodiments, the device 300 may be implanted perpendicular to an anterior posterior head axis of the patient. In other embodiments, the device 300 may be implanted parallel to an anterior posterior head axis of the patient. As shown in FIG. 10, the device 300 may be placed across the cranial vertex, such that the device 300 positions its contacts 300 to cover both hemispheres of the patient's skull. For example, the proximal end 305 of the electrode strip 302 may lie in one hemisphere (e.g., right side) of the patient's skull while the distal end 306 lies on the other hemisphere (e.g., left side) of the patient's skull. Although not shown in FIG. 10, it is also contemplated that the proximal end 305 of the electrode strip 302 may lie on the left side of the patient's skull while the distal end 306 lies on the right side of the patient's skull. The device 300 may be positioned such that at least one contact 300 is positioned on each hemisphere (e.g., right side or left side) of the patient's skull. Preferably, at least two to four contacts 303 may be positioned on each hemisphere of the patient's skull. Alternatively, more than one device 300 may be implanted in a subgaleal region between the skull and the scalp, and at or near the cranial vertex of the patient. In certain embodiments two or more devices 300 may be subgalleally implanted into the patient. For example, one device 300 may be implanted to cover one hemisphere of the patient's skull while a second device 300 is implanted to cover the other hemisphere of the patient's skull. More particularly, each device 300 may be positioned so as to broadly cover one hemisphere of the patient's skull.

The exemplary device 100, 200, 300 permits the subgaleal detection of epileptic events, minimizing and/or eliminating false positives, while detecting all or nearly all seizure events. By contrast, no techniques for long-term monitoring currently exist. The exemplary device 100, 200, 300 provides a small, safe, fully implantable chronic SG extracranial EEG monitoring system, which offers a safer approach to the analysis and treatment of epilepsy. In addition to providing immediate and accurate objective data corresponding to epileptic events, the exemplary device 100, 200, 300 also reduces the time and number of patients needed for drug or device trials by half or more, thereby reducing research, development and approval costs for such drugs and/or devices. In addition to reducing time, the device 100, 200, 300 also objectifies the data, thereby providing a new unbiased measurement not presently available to seizure therapy or experimental drug trials. In addition to its use for seizure detection, the device 100, 200, 300 may also be used in various areas of research and clinical management in current medical domains and in those domains in development including, but not limited to, sleep, psychiatry, physiology, and many other domains where chronic (long-term) EEG detection and analysis has relevance, as well as having immediate important biometric related applications for medicine, military, aerospace, biomedical clinical research, etc.

The exemplary device 100, 200, 300 may be used in combination with a therapeutic device directed to the treatment of seizures including, but not limited to, antiepileptic medications, implantable stimulators (e.g., electrical stimulators) and implantable drug delivery systems. Specifically, the device 100, 200, 300 may aid in monitoring the administration of medication to a patient by detecting breakthrough seizures and allowing for the timely collection of AED serum levels, as those skilled in the art will understand. The device 100, 200, 300 may also be used in conjunction with a device for monitoring recurring seizures, as those skilled in the art will understand. The device 100, 200, 300 may be programmed to distinguish between partial and generalized seizures in patients with partial epilepsy and also to distinguish between epileptic and non-epileptic seizures. The device 100, 200, 300 may quantify spike wave frequency and duration in patients with generalized epilepsies (e.g., absence epilepsy, JME, JAE, idiopathic GTCs, etc.). Furthermore, the device 100, 200, 300 may be used to rule out the diagnosis of epilepsy in a patient with an explained fall or loss of consciousness.

The device 100, 200, 300 may also identify a slowing of the EEG that occurs with cerebral ischemia, elevated intracranial pressure, or hypoperfusion (cardiac, non-cardiogenic syncope). The device 100, 200, 300 may record oscillatory EEG activity associated with normal cerebral functions such as movement, vision, and sensation. The resultant data may be employed in the afferent arm of a therapeutic feedback system (e.g., neuro-prosthesis). The device 100, 200, 300 may also record oscillatory EEG activity associated with abnormal cerebral functions such as tremor, tics, attentional issues, or behavioral abnormalities. The resultant data may be employed in the afferent arm of a therapeutic feedback system using pharmacological or electromagnetic stimulation. Still further, the device 100, 200, 300 may monitor depth of coma/sedation in patients undergoing long-term sedation in critical care settings. The device 100, 200, 300 may be used for the long-term monitoring of physiological brain rhythms including but not limited to sleep-related oscillations and transients for the purpose of research in human physiology, sleep and memory.

There are many modifications of the present invention which will be apparent to those skilled in the art without departing from the teaching of the present invention. For example, although the exemplary embodiments have been described with respect to the detection of seizures, the exemplary devices 100, 200, 300 may be used for the detection of other conditions (e.g., mood disorders such as depression, Parkinson's Disease, schizophrenia, sleep disorders, autism, etc.) without deviating from the scope of the invention. The embodiments disclosed herein are for illustrative purposes only and are not intended to describe the bounds of the present invention, which is to be limited only by the scope of the claims appended hereto.

EXAMPLE I

Figure 11:
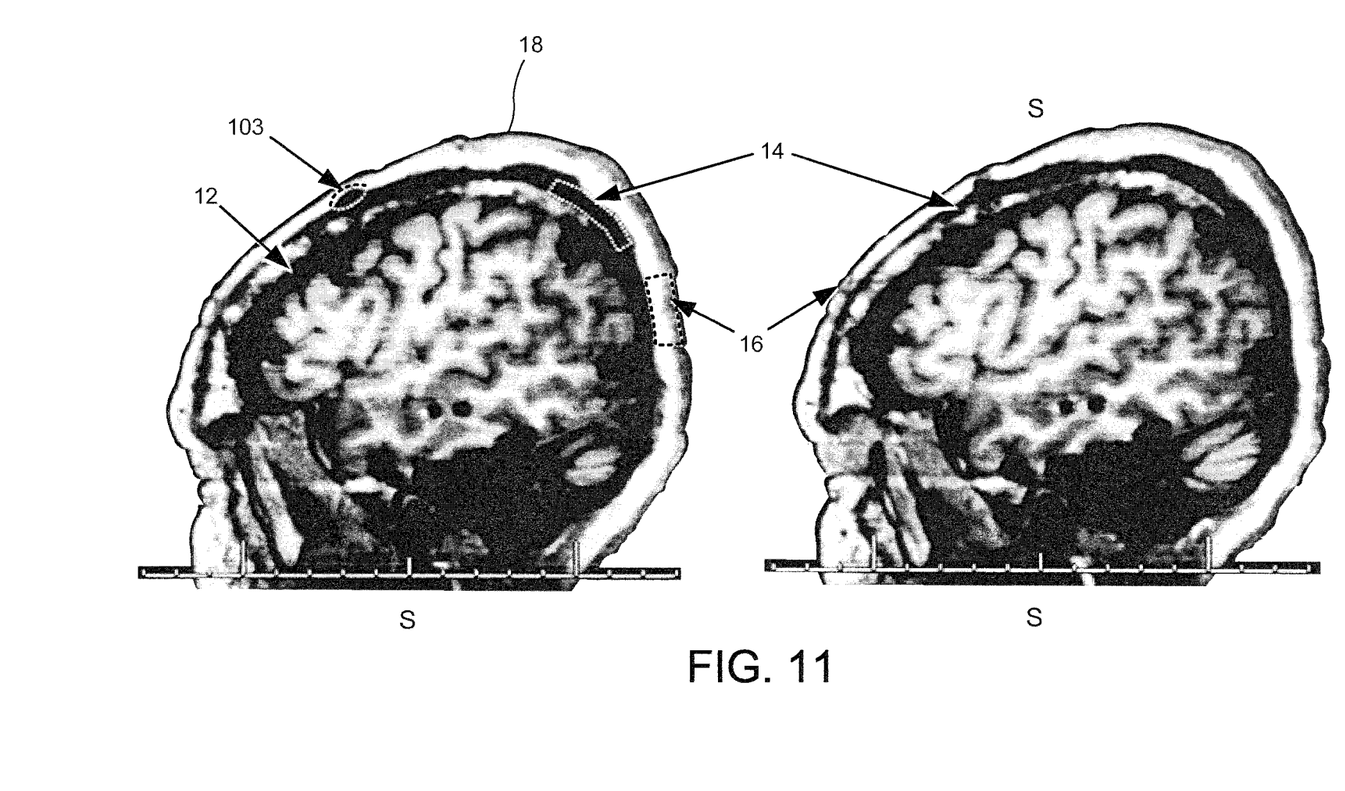
FIG. 11 shows an exemplary view of an exemplary device in an implanted configuration.

The exemplary device 100 may be implanted in a subgaleal region of a patient, near the brain, as shown in FIG. 11. As can be seen, at least one contact 103 (e.g., an electrode for recording electrophysiological data, particularly EEG data) of the device may be implanted in a subgaleal region that is between the skull 14 and the scalp 16 of the patient near the brain 12 of the patient. Specifically, the at least one contact 103 or electrode arrays 102, 102', 102" of the device 100 may be position perpendicular to a cranial vertex 18 of the patient. More particularly, the at least one contact 103 or electrode arrays 102, 102', 102" of the device 100 may lie across a mid-length of the patient's skull 14. It is contemplated that the exemplary device 200 may be alternatively implanted in the subgaleal region of the patient in the same manner described above and as shown in FIG. 11.

The device 100, 200 may be used to record EEG data from the patient extracranially without drilling through the patient's cranium for placement of any portion of the device 100, 200. The subgaleal device 100 provides a less invasive method as compared to electrodes implanted directly onto the dura mater that is also capable of detecting changes in the patient's EEG data to identify seizures within seconds of the start of the seizure episode. In this example, data recorded by the subgaleal device 100, 200 is compared to EEG data recorded by electrodes implanted directly onto the dura mater.

Figure 12:
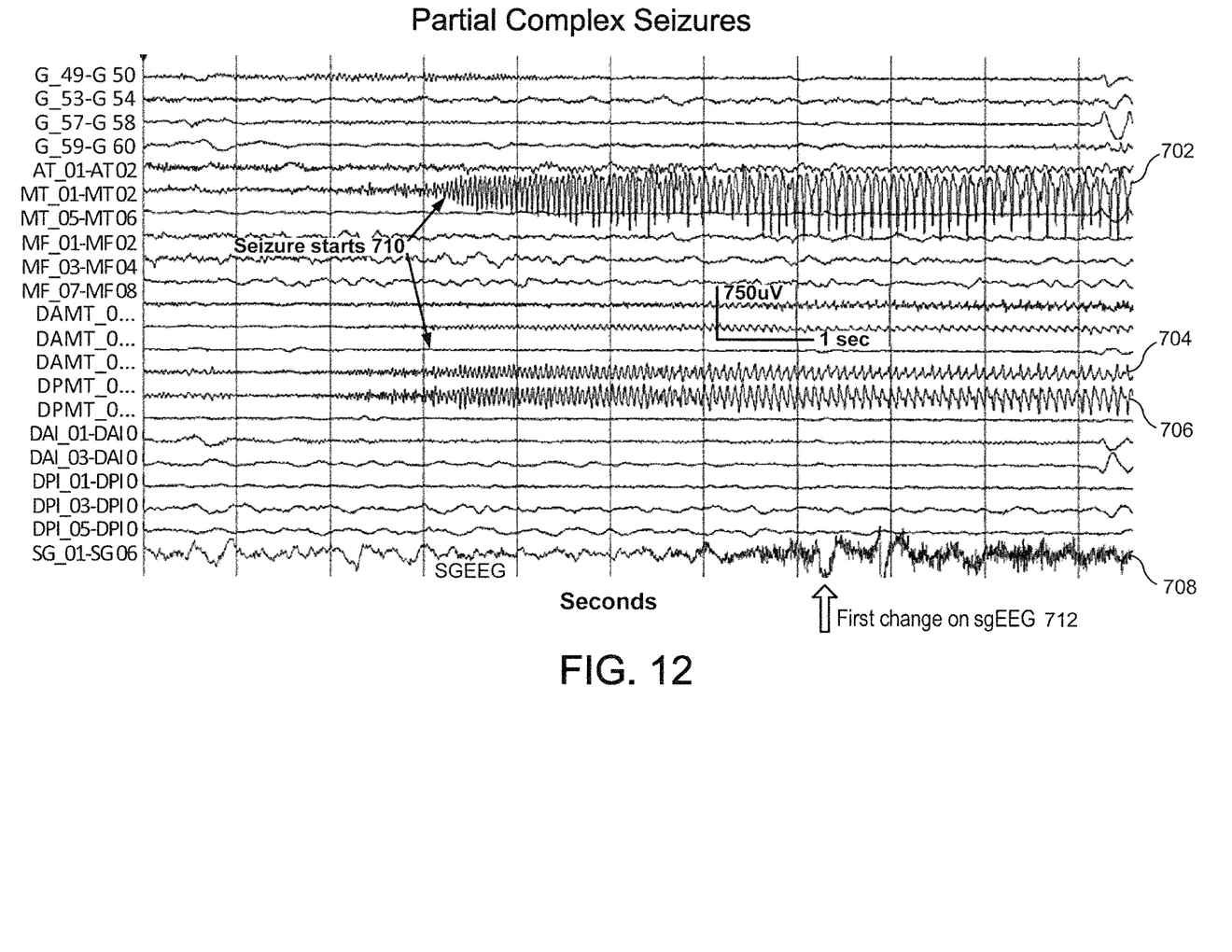
FIG. 12 shows EEG data recorded over time by electrodes implanted directly onto the dura mater and by an exemplary device implanted into a subgaleal region of a patient.

FIG. 12 shows the EEG data 702, 704, 706 recorded over time in a patient suffering from a partial complex seizure by electrodes implanted directly onto the dura mater as well as EEG data 708 recorded by an exemplary subgaleal device 100, 200 of the present invention. In a particular embodiment, the at least one contact 103 or electrode arrays 102, 102', 102" of the device 100 may be position acrossed the vertex. Although this particular example refers to partial complex seizure, it is understood that the subgaleal device 100, 200 of the present invention may be used to detect any number of neurological disorders and other types of seizures. As shown at reference number 710, an excessive level of neurological activity may be record in EEG data 702, 704, 706 recorded by the electrodes implanted into the dura mater and signifies the onset of a seizure. The subgaleal device 100, 200 of the present invention may also be used to detect the onset of the seizure. As can be seen in FIG. 12, the EEG data 708 recorded by the subgaleal device 100, 200 may detect a deviation 712 from baseline signal characteristics within seconds, e.g., less than 5 seconds, of the onset of the seizure as recorded by the electrodes implanted into the dura mater. The EEG data 708 shown in FIG. 12 demonstrates that the subgaleal device 100, 200 may detect the onset of the seizure within approximately 3 seconds. The EEG data 708 recorded by the subgaleal device 100, 200 may be processed using any suitable seizure detection algorithm or may be visually examined by a physician to identify a seizure. The seizure detection algorithm may be executed by a processor 106 or may be part of a remote processing arrangement that receives the EEG data 708 recorded by the subgaleal device 100, 200. In certain embodiments, the seizure detection algorithm analyzes the EEG data 708 in real-time. Further, upon detection of a seizure, the subgaleal device 100, 200 may trigger an anti-seizure and/or anti-epileptic treatment. In particular, the subgaleal device 100, 200 may trigger an anti-seizure and/or anti-epileptic treatment immediately upon detection of the onset of a seizure. For example, the anti-seizure and/or anti-epileptic treatment may be administered in less than 5 seconds, within 3 seconds of the onset of the seizure.

The exemplary embodiments described and claimed herein is not to be limited in scope by the specific embodiments herein disclosed since these embodiments are intended as illustrations. Any equivalent embodiments are intended to be within the scope of this application. Indeed, various modifications in addition to those shown and described herein will become apparent to those skilled in the art from the foregoing description. Such modifications are also intended to fall within the scope of the appended claims. All publications cited herein are incorporated by reference in their entirety.

What is claimed is:

1. A system for detecting onset of a seizure in a patient, comprising
    an implantable body configured for implantation in a subgaleal extracranial space of the patient, the implantable body comprising:
    (a) a first electrode array configured for implantation entirely within the subgaleal extracranial space, the first electrode array including a first elongated body comprising first and second electrode contacts separated from one another by a first distance selected to facilitate the detection by the first electrode array from the subgaleal extracranial space of ictal brain electrical activity while minimizing noise; and
    (b) a unit configured for implantation entirely within the subgaleal extracranial space and coupled to the first electrode array and including:
        a processor analyzing data corresponding to the brain electrical activity detected by the first electrode array from the subgaleal extracranial space to determine whether an epileptic event has occurred and generating epileptic event data based on this determination, and
        a transceiver controlled by the processor to wirelessly transmit epileptic event data to and from a remote computer.

2. The system of claim 1, wherein the processor is configured to continuously analyze data corresponding to the brain electrical activity detected by the first electrode array.

3. The system of claim 1, wherein the implantable body further comprises a battery.

4. The system of claim 1, wherein the first electrode array is sized and shaped for insertion at a cranial vertex.

5. The system of claim 1, wherein the first electrode array includes a reinforced portion.

6. The system of claim 1, further comprising a memory coupled to the processor, the memory storing one or more of epileptic event data and patient biometric data.

7. The system of claim 1, further comprising a pressure sensor embedded on the first electrode array.

8. The system of claim 1, further comprising a biometric sensor embedded on the first electrode array, the biometric sensor capturing one or more of pulse, blood oxygenation data, motion, acceleration, galvanic resistance, temperature, electro-myographic data and rheologic changes.

9. The system of claim 1, further comprising:
    (c) a second electrode array configured for implantation in the subgaleal extracranial space, the second electrode array including a second elongated body comprising third, fourth and fifth electrode contacts separated from one another by a second distance selected to facilitate the detection by the second electrode array from the subgaleal extracranial space of ictal brain electrical activity while minimizing noise; and
    (d) a third electrode array configured for implantation in the subgaleal extracranial space, the third electrode array including a third elongated body comprising sixth, seventh and eighth electrode contacts separated from one another by a third distance selected to facilitate the detection by the third electrode array from the subgaleal extracranial space of ictal brain electrical activity while minimizing noise.

10. The system of claim 9, wherein the second distance is approximately 6 cm and wherein the third distance is approximately 6 cm.

11. The system of claim 1, wherein the first, second and third electrode arrays are connected to the unit by first, second and third wires.

12. The system of claim 1, wherein the implantable body is adapted to identify brain wave data corresponding to seizures that have no external or behavioral manifestations.

13. The system of claim 1, wherein the implantable body includes a central axis bisecting the length of the implantable body, the first electrode configured to be positioned proximal of the central axis in an operative configuration and the second electrode configured to be positioned distal of the central axis in the operative configuration.

14. The system of claim 1, wherein the implantable body includes a proximal end and a distal end, the unit being positioned at the proximal end of the implantable body.

15. The system of claim 14, wherein the implantable body further comprises a housing hermetically sealed around the unit.

16. The system of claim 1, wherein the first electrode array detects the brain electrical activity only from the subgaleal extracranial space of the patient.

17. The system of claim 1 wherein the first distance is approximately 6 cm.

18. A method for capturing brain wave data, comprising:
    inserting, using a minimally invasive surgical technique, an implantable body into a subgaleal extracranial space of a patient with the implantable body positioned entirely within the subgaleal extracranial space along a cranial surface, wherein first and second electrode contacts of a first electrode array of the implantable body are positioned to face the cranium, the first and second electrode contacts being separated from one another by a first distance selected to facilitate detection of ictal brain activity while minimizing noise;

detecting brain electrical activity using the first and second electrode contacts from the subgaleal extracranial space;

monitoring and analyzing, via a processor, the brain electrical activity detected from the subgaleal extracranial space to identify epileptic events; and transmitting epileptic event data corresponding to an identified epileptic event to one of a remote computer, local computer, local base station, cellular phone, portable tablet, personal computing device and cloud storage.

19. The method of claim 18, wherein the epileptic event data is transmitted immediately upon detection of the corresponding epileptic event.

20. The method of claim 18, wherein the epileptic event data is transmitted at predetermined intervals and stored in a memory.

21. The method of claim 18, wherein the epileptic event data is transmitted when an amount of data stored in the memory reaches a predetermined percentage of a capacity of the memory.

22. The method of claim 18, further comprising detecting biometric data corresponding to one or more of pulse, blood oxygenation data, motion, acceleration, galvanic resistance, temperature, electro-myographic data and rheologic changes.

23. The method of claim 18, wherein the first electrode array is positioned at a cranial vertex.

24. The method of claim 18, wherein the first distance is approximately 6 cm.

25. A method for detecting onset of a seizure in a brain of a patient, comprising:

obtaining, from a plurality of electrodes implanted entirely within an extracranial subgaleal space of the patient and positioned in contact with a cranial surface of the patient, brain electrical activity data detected by the electrodes from the extracranial subgaleal space corresponding to electrophysiological signals produced by the brain, wherein first and second ones of the electrodes are separated from one another by a distance selected to facilitate detection of ictal brain electrical activity;

continuously monitoring and analyzing, via a processor, the brain electrical activity data to identify the onset of the seizure in the brain, the processor being within a unit configured for implantation entirely within the subgaleal extracranial space; and administering an anti-seizure treatment to the patient when the processor identifies the onset of the seizure in the brain.

26. The method of claim 25, wherein the anti-seizure treatment is administered within 5 seconds of the onset of seizure in the brain.

27. The method of claim 25, wherein the anti-seizure treatment comprises administration of an anti-epileptic medication or an electrical stimulation.

28. The method of claim 25, wherein the first distance is approximately 6 cm.

* * * * *